United States Patent [19]
Winters

[11] Patent Number: 4,954,508
[45] Date of Patent: Sep. 4, 1990

[54] PHARMACOLOGICALLY ACTIVE PYRAZOLOPYRIDINES

[75] Inventor: Giorgio Winters, Arese, Italy

[73] Assignee: Gruppo Lepetit S.p.A., Milan, Italy

[21] Appl. No.: 286,917

[22] Filed: Dec. 20, 1988

Related U.S. Application Data

[63] Continuation-in-part of Ser. No. 562,796, Dec. 19, 1983, abandoned.

[30] Foreign Application Priority Data

Dec. 20, 1982 [GB] United Kingdom ............... 8236131

[51] Int. Cl.$^5$ ................... A61K 31/44; C07D 471/04
[52] U.S. Cl. ................................... 514/303; 546/120
[58] Field of Search .................... 546/120; 514/303

[56] References Cited

U.S. PATENT DOCUMENTS 4,020,072  4/1977  Hoehn ............................ 546/120
4,532,248  7/1985  Franchowick et al. ......... 514/302

FOREIGN PATENT DOCUMENTS 8322270  7/1988  Australia .
2128186A 4/1984  United Kingdom .

Primary Examiner—Mary C. Lee
Assistant Examiner—Bernard I. Dentz
Attorney, Agent, or Firm—Stephen L. Nesbitt

[57] ABSTRACT

The present invention is directed to new 4,7-dihydropyrazolo[3,4-b]pyridines. The compounds possess $Ca^{2+}$-antagonist, antihypertensive, vasodilating and antiangina activity. A process for producing them as well as pharmaceutical compositions containing them are also described.

7 Claims, No Drawings

PHARMACOLOGICALLY ACTIVE PYRAZOLOPYRIDINES

This is a continuation-in-part of application Ser. No. 562,796, filed Dec. 19, 1983 now abandoned.

The present invention is directed to a class of pharmacologically active 4,7-dihydropyrazolo[3,4-b]pyridines of formula

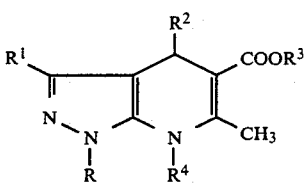

wherein

R represents hydrogen, ($C_1$–$C_6$)alkyl, ($C_1$–$C_6$)alkenyl, ($C_3$–$C_7$) cycloalkyl, phenyl which is optionally substituted by 1, 2 or 3 substituents selected from ($C_1$–$C_4$)alkyl, halo($C_1$–$C_4$)alkyl, ($C_1$–$C_4$)alkoxy, chloro, fluoro, bromo, nitro, and ($C_1$–$C_6$)alkoxycarbonyl, or phenyl($C_1$–$C_4$)alkyl, wherein the phenyl group is optionally substituted as above;

$R^1$ represents hydrogen, ($C_1$–$C_6$)alkyl, ($C_1$–$C_6$)alkenyl, ($C_3$–$C_7$)cycloalkyl, ($C_1$–$C_6$)alkoxycarbonyl, phenyl optionally substituted as above, or phenyl($C_1$–$C_4$)alkyl, optionally substituted as above;

$R^2$ represents phenyl groups optionally substituted with 1, 2 or 3 substituents selected from ($C_1$–$C_4$)alkyl, ($C_1$–$C_4$)alkoxy, halo($C_1$–$C_4$)alkyl, chloro, bromo, fluoro, nitro, cyano, ($C_1$–$C_6$)alkoxycarbonyl, and a group of formula $S(O)_n$—($C_1$–$C_6$)alkyl, wherein n represents zero or the integer 1 or 2, or $R^2$ represents a pentafluorophenyl group, an α- or β-naphthyl group, an aromatic 5–6 membered heterocycle ring such as furanyl or thienyl, a group of formula

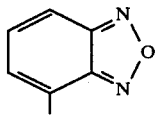

or a group of formula

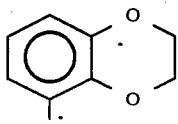

$R^3$ represents ($C_1$–$C_6$)alkyl, ($C_1$–$C_6$)alkenyl, phenyl optionally substituted as above, and phenyl($C_1$–$C_4$)alkyl optionally substituted as above, ($C_1$–$C_4$)alkoxy($C_1$–$C_6$)alkyl, amino($C_1$–$C_6$)alkyl, mono-or di-($C_1$–$C_4$)alkylamino($C_1$–$C_6$)alkyl, or a group

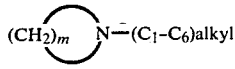

wherein m is an integer selected from 3, 4, and 5, and one of the —$CH_2$— groups can be replaced by a heteroatom selected from O, S, and N;

$R^4$ represents hydrogen, ($C_1$–$C_4$)alkyl or benzyl; and the physiologically acceptable salts thereof.

($C_1$–$C_6$)alkyl groups, as defined in the present application, includes: methyl, ethyl, propyl, isopropyl, n-butyl, isobutyl, pentyl, hexyl, and the like.

($C_3$–$C_7$)cycloalkyl groups, are: cyclopropyl, cyclobutyl, cyclopentyl, cyclohexyl, and cycloheptyl groups.

($C_1$–$C_6$)alkoxy groups includes: methoxy, ethoxy, propoxy, butoxy, pentoxy, and hexoxy groups.

($C_1$–$C_4$)alkyl groups and ($C_1$–$C_4$)alkoxy groups are groups of 1 to 4 carbon atoms, inclusive, which are included in the above definition of ($C_1$–$C_6$)alkyl groups and ($C_1$–$C_6$)alkoxy groups, respectively.

The term "halo" represents halogen atoms selected from chloro, bromo, and fluoro, while halo($C_1$–$C_4$)alkyl groups are halogenalkyl groups of 1 to 4 carbon atoms inclusive, wherein some or all the hydrogen atoms are replaced with halogen atoms. Representative examples of halo($C_1$–$C_4$)alkyl groups are: trifluoromethyl, chlorodifluoromethyl, bromochlorofluoromethyl, trichloromethyl, 1,1-dichloroethyl 1,2-dichloroethyl, 1-chloro-2,2,2-trifluoroethyl, and the like.

"Physiologically acceptable salts" are pharmaceutically acceptable salts wherein the whole toxicity of the compound is not increased compared with the non-salt. These acid addition salts are obtained by treating compounds of the above formula I with pharmaceutically acceptable acids.

Representative examples of acids suitable for the formation of physiologically acceptable salts are: hydrohalide, sulfuric, phosphoric, and nitric acids; aliphatic, alicyclic, aromatic or heterocyclic carboxylic or sulphonic acids, such as formic, acetic, propionic, succinic, glycolic, lactic, malic, tartaric, citric, ascorbic, α-ketoglutaric, glutamic, aspartic, maleic, hydroxymaleic, pyruvic acid; phenylacetic, benzoic, para-aminobenzoic, anthranilic, para-hydroxybenzoic, salicylic, para-aminosalicylic or embonic acid, methanesulfonic, ethanesulfonic, hydroxyethanesulfonic, ethylenesulfonic acid; halobenzenesulfonic, toluenesulfonic, naphthalenesulfonic acids or sulfanilic acid.

These or other salts of the new compounds may also be used for purifying the resulting compounds by converting them into salts, isolating the latter and liberating the free compound from them. When according to the above outlined procedures, compounds of formula I are obtained as the corresponding salts of pharmaceutically acceptable acids, they may be converted into the corresponding free base by treatment with an alkali agent.

The free base may in turn be transformed into the corresponding salts by reaction with predetermined pharmaceutically acceptable acids. In view of the close relationship between the new compounds in the free form and in the form of their salts what has been said above and hereinafter with reference to the free compounds concerns also the corresponding salts.

A preferred group of compounds of the present invention are those of formula I wherein R and $R^1$ independently are hydrogen, ($C_1$–$C_6$)alkyl or phenyl, unsubstituted or substituted as above, $R^2$ is a phenyl group substituted by 1 or 2 substituents, selected from nitro, ($C_1$–$C_4$)alkoxy, ($C_1$–$C_4$)alkyl, chloro or trifluoro methyl, $R^3$ is ($C_1$–$C_6$)alkyl or ($C_1$–$C_4$)alkoxy($C_1$–$C_4$)alkyl, and $R^4$ is hydrogen, methyl or benzyl, or a corresponding physiologically acceptable acid addition salt.

Another preferred group of compounds are those compounds of formula I wherein R is hydrogen, methyl or phenyl, optionally substituted as above, $R^1$ is hydrogen, methyl, ethyl, isopropyl, phenyl optionally substituted as above, $R^2$ is 2- or 3-nitrophenyl, 2- or 3-methylphenyl, or 2- or 3-trifluoromethylphenyl, $R^3$ is $(C_1-C_6)$alkyl, $(C_1-C_4)$alkoxy$(C_1-C_6)$alkyl, and $R^4$ is hydrogen, or a corresponding physiologically acceptable acid addition salt.

An outline of the process for the production of the compounds of the invention is the following:

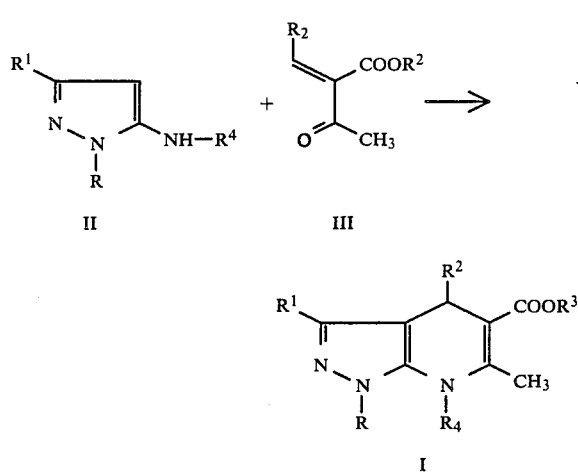

A 5-aminopyrazole derivative of formula II, wherein R, $R^1$ and $R^4$ are defined as above, is reacted with a substituted α,β-unsaturated ketoester of formula III, also named 2-vynilidenacetoacetate, wherein the substituents are as above.

This reaction can be carried out employing different molar proportions of the two reactants, however an equimolar proportion or a slight excess of the aminopyrazole reactant is preferred.

The reaction solvent is an organic solvent which does not unfavourably interfere with the reaction course. Representative examples of such solvents are: $(C_1-C_4)$alkanols such as methanol, ethanol, propanol, isopropanol, and t-butanol and the like, glycols and their ethers. One of the preferred ether-glycols is the mono-methyl ether of the ethylene glycol (methylcellosolve ®).

The reaction temperature is generally between 40° C. and the reflux temperature.

The reaction time obviously varies considerably depending on the reaction conditions, however, the reaction is generally complete in 15 minutes to 20-60 hours. In any case, the reaction course can be monitored by means of the usual techniques such as TLC using a suitable eluting mixture such as methanol/chloroform 1:9 or n-hexane/ethanol 8:2. Based on these data the skilled man is able to optimize the reaction conditions, and in particular the reaction time.

Alternatively, at least in some instances, the dihydropyrazolopyridines of the invention can be prepared by reacting a 5-aminopyrazole derivative with about an equimolar proportion of an aldehyde of formula $R^2$—CHO and an acetoacetic acid ester of formula $CH_3COCH_2COOR^3$, wherein $R^2$ and $R^3$ are as above, in an organic solvent, preferably a lower alkyl alcohol. In any case the reaction is preferably carried out under nitrogen stream and in the dark. The work up procedures include: extraction with solvents, precipitation by non-solvents, purification by chromatography, especially flash-chromatography, and crystallization.

The compounds of formula I wherein $R^4$ is as above but different from hydrogen, can also be obtained by reacting the corresponding compound of formula I wherein $R^4$ is hydrogen with a suitable alkylating agent.

Representative examples of suitable alkylating agents include: lower alkyl or optionally substituted benzyl chlorides, bromides or iodides.

The starting materials of formula II

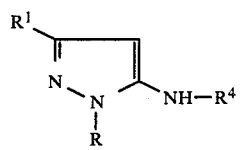

are prepared essentially by following the techniques known for the preparation of 5-pyrazolamines and described in reference books such as "The Chemistry of heterocyclic compounds", Vol. XX, pages 41-43, Wiley and Wiley publisher, New York, 1964.

More particularly, when $R^4$ is different from hydrogen, they can be prepared according to Micaelis, Annales der Chemie, 339, 117 (1905), and Micaelis et al., Berichte der Org. Chem. 40, 4488, which describes techniques which are well known in the art.

The above starting materials wherein the substituent at position "5" is benzylamine, i.e. $R^4$ is benzyl, or substituted benzyl, can be prepared reacting the corresponding derivative wherein $R^4$ is hydrogen with benzyl chloride, bromide, or iodide. Suitable reaction solvents are organic solvents such as benzene, toluene, chloroform, dimethylformamide, and methylene chloride. The reactants are usually contacted in equimolar proportions in the presence of an excess of a tertiary amine such as trimethylamine and triethylamine or an inorganic base.

The preparation of the 2-vynilidenacetoacetate derivatives of formula III is known from the chemical literature.

The compounds of the invention possess pharmacological activity and therefore they can be used as medicines. With the term "use" all industrial applicable aspect and acts of said use, including their embodying into pharmaceutical compositions are intended.

In particular, the compounds of the invention show in vitro calcium-antagonist activity and in vivo antihypertensive action. The possible therapeutic indications include therefore the anti-angina and vasodilating indications.

The in vitro activity can be ascertained by means of a test for antagonism of the calcium-induced contractions in $K^+$-depolarized taenia of the Guinea-pig caecum.

According to the above technique, strips of taenia (1-2 mm diameter, 2-2.5 cm relaxed length), were dissected from the caecum of male guinea-pigs (250-350 g) and set up in 20 ml isolated-organ baths containing $K^+$-depolarizing Tyrode solution maintained at 35° C. and gassed with 95% $O_2$ and 5% $CO_2$. The composition of the $K^+$-Tyrode solution was (mmol/l): NaCl 97; KCl 40; $NaHCO_3$ 11.9; $NaH_2PO_4$ 0.4; glucose 5.5; pH 7.1. Contractile responses were measured under isotonic conditions (1 g load) using a Harvard isotonic transducer connected to a Rikadenki potentiometric recorder.

Cumulative concentration-response curves were obtained to $CaCl_2$ (30–3,000 μmol/l) by increasing the $Ca^{2+}$ concentration at 3 min intervals in logarithmic increments /Van Rossum, Arch. Int. Pharmacodyn., 143 299–330, 1963/. A 20 min wash-out period (6 changes of bathing fluid) was allowed between curves. The 100% response was taken as the maximum contractile response of the tissue during the second concentration-response curve, and all subsequent contractions were calculate as a percentage of this value. Dose ratios were calculated as the ratio of the concentration of $Ca^{2+}$ which produced a 50% maximal response ($EC_{50}$) in the presence and absence of the antagonist. Apparent $pA_2$ values were calculated by the method of Arunlakshana and Schild, Br. J. Pharmac. Chemother., 14, 48–58, (1959), by plotting log (dose ratio-1) against negative log (molar concentration antagonist). Student's test was used for comparison of mean values. Values in the text refer to mean ± SEM. All concentrations are the final concentration of drug in the bathing solution.

The compounds are initially tested at a fixed concentration (10 μg/ml). In these conditions the compounds of the invention shows antagonism of $Ca^{2+}$ induced contractions in $K^+$-depolarized taenia. More particularly, the compounds of Examples 1, 2, 11, 13, 18, 27, 35, 39, 41, 42, and 43 show a $pA_2$ value in the range 8.2–9, cause concentration-dependent displacement to the right of cumulative concentration-response curves to $Ca^{2+}$, have a rapid onset of action, and cause a rapid relaxation of $Ca^{2+}$ (300 μM)- induced contractions at low concentrations (0.01–0.1 μM).

The in vivo activity can be ascertained by means of the so-called "pithed rat preparation".

The rats are infused with angiotensin II in order to evaluate the blood pressure.

The procedure allows evaluation of hypotensive effects in the absence of autonomic reflexes.

The compounds of the invention produce dose-dependent depression of blood pressure, without affecting heart rate. The compounds in this test are administered either intraveneously or intraduodenally.

According to the above technique, male Sprague-Dawley rats (250–330 g) were anaesthetized with sodium pentobarbitone (40–50 mg/kg, i.p.), pithed and respired with oxygen. Body temperature was maintained between 35.0° and 36.5° C. Blood pressure was measured from the left carotid artery and the antagonists were administered cumulatively via the left jugular vein or via a cannula placed in the duodenum. Blood pressure was maintained between 75–120 mmHg by an intraveneous infusion of angiotensin II (0.2–1.0 μg/kg/min). Heart rate was calculated from the ECG.

In the above test, the compound of Example 1 shows a very significant dose-dependent depression of blood pressure, at a dose of 0.1–3 μmol/kg, i.v., and did not cause second degree atrioventricular block at any dose-level tested.

The cardiovascular activity of the compounds of the invention was demonstrated also in the spontaneously hypertensive rats described by K. Aoki in the Japan Cir. Journal, Vol. 27, p. 289, (1963). The arterial pressure was evaluated according to H. Friebel, E. Vredom, as described in Arch. Exp. Phat. Pharmak., Vol. 232, p. 416 (1958).

Some of the compounds of the invention show a lowering of the arterial pressure of at least 15% when administered at a dose inferior to 1/10 of the $LD_{50}$. This 15% threshold is generally considered predictive of significant cardiovascular activity.

Table I summarizes the results obtained in this test for some representative compounds of formula I:

TABLE I

| Compound of example No. | dose (i.p.) mg/Kg | % drop of the blood pressure |
|---|---|---|
| 1 | 30 | 20 |
| 11 | 30 | 17 |
| 13 | 30 | 46 |
| 15 | 25 | 50 |
| 16 | 30 | 37 |
| 27 | 30 | 47 |
| 29 | 30 | 39 |
| 30 | 30 | 21 |
| 35 | 20 | 19 |
| 36 | 30 | 32 |
| 38 | 30 | 34 |
| 41 | 3 | 37 |
| 51 | 30 | 36 |
| 53 | 40 | 24 |
| 55 | 10 | 33 |

These results were confirmed in renal hypertensive dogs where significant drops of the systolic blood pressure are observed upon oral administration of the compounds of the invention.

The results obtained in the above test by representative compounds of the invention are summarized in Table II, below:

TABLE II

| Compounds of example No. | Dose (os) mg/Kg | % drop of the blood pressure |
|---|---|---|
| 15 | 10 | 32 |
|  | 1 | 15 (lasting for about 5 h) |
| 16 | 10 | 21 |
| 27 | 3 | 40 (lasting for 5–7 h) |
| 35 | 1 | 38 (lasting for about 7 h) |
| 36 | 10 | 36 |
|  | 0.3 | 19 |
| 41 | 0.1 | 33 |
| 51 | 3 | 35 |
| 53 | 3 | 53 |
| 55 | 3 | 26 |

Generally the compounds of the invention possess prolonged duration of action.

In fact representative examples possess a duration of antihypertensive action on animals of 8 to 12 h or more at a doses equal to the $ED_{50}$ value.

The compounds may be administered in various manners to achieve the desired effect. The compounds may be administered alone or in the form of pharmaceutical preparations to the patient being treated either orally or parenterally, such as, intraveneously or intramuscularly. The formulation of suitable pharmaceutical compositions can be carried out by the skilled man according to the general common knowledge in the art, and referring to reference books, such as the "Remington's Pharmaceutical Sciences" Handbook, Mack Publishing Company, U.S.A.

The amount of compound administered will vary with the severity of the hypertension, and the mode of administration. For oral administration the antihypertensively effective amount of compound is from about 0.01 mg/kg (milligrams per kilograms) of patient body weight per day to about 10 mg/kg of patient body weight per day and preferably from about 0.05 mg/kg of patient body weight per day to about 5 mg/kg of patient body weight per day.

For parenteral administration the antihypertensively effective amount of compound is from about 0.001 mg/kg of patient body weight per day up to about 5 mg/kg of patient body weight per day and preferably from about 0.01 mg/kg of patient body weight per day up to about 2 mg/kg of patient body weight per day.

For oral administration a unit dosage may contain, for example, from 0.50 to 100 mg of the active ingredient. For parenteral administration a unit dosage may contain, for example, from 0.05 to 70 mg of the active ingredient. Since the compounds of the invention generally possess a long lasting duration of action they might be conveniently administered once or twice a day, however, repetitive daily administrations may be, at least in some instances, desirable and will vary with the conditions of the patient and the mode of administration. As used herein, the term "patient" is taken to mean a warm blooded animal, humans included.

For oral administration the compounds can be formulated into solid or liquid preparations such as capsules, pills, tablets, troches, powders, solutions, suspensions or emulsions. The solid unit dosage forms can be a capsule which can be of the ordinary gelatin type, either hard or soft, containing for example lubricants and inert fillers, such as lactose, sucrose and cornstarch. In another embodiment the compounds of the invention can be tabletted with conventional tablet bases such as lactose, sucrose and cornstarch in combination with binders, such as acacia, cornstarch or gelatin, disintegrating agents such as potato starch or alginic acid, and a lubricant such as stearic acid or magnesium stearate.

For parenteral administration the compounds may be administered as injectable dosages of a solution or suspension of the compound in a physiologically acceptable diluent with a pharmaceutical carrier which can be a sterile liquid such as water and oils with or without the addition of a surfactant and other pharmaceutically acceptable adjuvants. Illustrative of oils which can be employed in these preparations are those of mineral petroleum, animal, vegetable or synthetic origin. For example, peanut oil, soybean oil and mineral oil. In general, water, saline, aqueous dextrose and related sugar solutions, ethanol and glycols such as propylene glycol or polyethylene glycol can be used as liquid carriers for injectable solutions.

For rectal administration the compounds are administered in the form of suppositories, admixed with conventional vehicles such as, for example, cocoa butter, wax, spermaceti, polyvinylpyrrolidone, or polyoxyethylenglycols and their derivatives.

The compounds can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, a silicon rubber manufactured by the Dow-Corning Corporation. The oral route is generally the preferred route of administration of the compounds of the invention, while the capsule is generally the preferred pharmaceutical formulation.

The following are illustrative pharmaceutical formulations which may be employed in practicing the present invention:

A capsule is prepared with:

| | |
|---|---|
| 4,7-Dihydro-1,3,6-trimethyl-4-(2-nitrophenyl)-1H-pyrazolo[3,4-b]pyridin-5-carboxylic acid methyl ester | 50 mg |
| Saccharose | 10 mg |
| Polyvinylpyrrolidone | 2 mg |
| Sodium dioctylsulfosuccinate | 0.5 mg |
| Magnesium stearate | 2.5 mg |
| Corn starch | q.s. to 150 mg | tablet is prepared with:

| | |
|---|---|
| 4,7-Dihydro-1,3,6-trimethyl-4-(2-nitrophenyl)-1H-pyrazolo[3,4-b]pyridin-5-carboxylic acid methyl ester | 100 mg |
| Saccharose | 30 mg |
| Polyvinylpyrrolidone | 5 mg |
| Sodium dioctylsulfosuccinate | 1.4 mg |
| Magnesium stearate | 8 mg |
| Corn starch | q.s. to 250 mg | sugar coated tablet is prepared with:

| | |
|---|---|
| 4,7-Dihydro-1,3,6-trimethyl-4-(2-nitrophenyl)-1H-pyrazolo[3,4-b]pyridin-5-carboxylic acid methyl ester | 50 mg |
| Polyvinylpyrrolidone | 2 mg |
| Sodium carboxymethylcellulose | 1.5 mg |
| Avicel ® | 5 mg |
| Titanium dioxide | 2 mg |
| Magnesium stearate | 2.5 mg |
| Corn starch | 8 mg |
| Gum arabic | 5 mg |
| Talc | 10 mg |
| Kaolin | 2 mg |
| Saccharose | q.s. to 150 mg |

The following examples are intended to further illustrate the present invention, but, as such, cannot be construed as limiting the scope of the invention.

EXAMPLE 1

4,7-dihydro-1,3,6-trimethyl-4-(2-nitrophenyl)-1H-pyrazolo[3,4-b]pyridin-5-carboxylic acid methyl ester.

Methyl-2-(2-nitrobenzyliden)acetoacetate (10 g; 0.040 mol) is added to 1,3-dimethyl-5-pyrazolamine (4.89 g; 0.044 mol) in ethanol (40 ml) The mixture is refluxed for about 5 hours, then the solvent is evaporated under reduced pressure and the residue is taken up in ethyl ether and recovered by filtration. M.p. 216°–220° C.

EXAMPLE 2

4,7-dihydro-1,3,6-trimethyl-4-(2-nitrophenyl)-1H-pyrazolo[3,4-b]pyridin-5-carboxylic acid ethyl ester.

The reaction is carried out essentially as above, using ethyl-2-(2-nitrobenzyliden)acetoacetate and refluxing for about 3 hours. M.p. 194°–198° C.

EXAMPLE 3

4,7-dihydro-1,3,6-trimethyl-4-(3-nitrophenyl)-1H-pyrazolo[3,4-b]pyridin-5-carboxylic acid methyl ester.

1,3-Dimethyl-5-pyrazolamine (3.33 g; 0.030 mol) is dissolved in ethanol (35 ml) and methyl-2-(3-nitrobenzyliden)acetoacetate (6.75 g; 0.27 mol) is added thereto. The mixture is refluxed for about 5 hours, then the solvent is evaporated under reduced pressure and the residue is taken up in methylene chloride, washed with 2% hydrochloric acid and then with saturated aqueous sodium bicarbonate, the organic phase is dried over sodium sulphate and then the solvent is evaporated. The solid compound of the title is recovered by filtration, after taking up in ethyl ether. M.p. 163°–166° C.

EXAMPLE 4

4,7-dihydro-1,3,6-trimethyl-4-phenyl-1H-pyrazolo[3,4-b]pyridin-5-carboxylic acid ethyl ester, hydrochloride.

Ethyl-2-benzylidenacetoacetate (50 mmol) is added to 1,3-dimethyl-5-pyrazolamine (0.050 ml) in ethanol (40 ml)

The mixture is refluxed for about 3 hours. The solvent is evaporated and the residue is taken up in ethyl ether, collected by filtration, and dried. The obtained solid is then dissolved in methanol and a mixture of hydrochloric acid/methanol (45 mmol of HCl) is added thereto; the product of the title precipitates by addition of ethyl ether. M.p. 232° C. (dec.).

EXAMPLE 5

4,7-dihydro-1,3,6-trimethyl-4-(2-methylphenyl)-1H-pyrazolo[3,4-b]pyridin-5-carboxylic acid ethyl ester, hydrochloride.

1,3-Dimethyl-5-pyrazolamine (0.050 mol) in ethanol (50 ml) is added with ethyl-2-(2-methylbenzyliden)acetoacetate (0.050 mol). The mixture is refluxed for about 90 minutes, then, after cooling to room temperature, further ethyl-2-(2-methylbenzyliden)acetoacetate (0.050 mol) is added thereto and the temperature is raised again to the reflux temperature and heating is continued for further 90 minutes. The reaction mixture is then cooled, the solvent is evaporated, and residue is taken up in ethyl ether, collected by filtration and dried. The solid is then worked up as in the above example to give the product of the title. M.p. 235° C. (dec.).

By operating essentially as above, the following compounds are obtained, starting from the suitable reactants.

EXAMPLE 6

4,7-dihydro-1,3,6-trimethyl-4-(3-methoxyphenyl)-1H-pyrazolo[3,4-b]pyridin-5-carboxylic acid ethyl ester, hydrochloride.

Starting from 1,3-dimethyl-5-pyrazolamine and ethyl-2-(3-methoxybenzyliden)acetoacetate. M.p. 200°–202° C.

EXAMPLE 7

4,7-dihydro-1,3,6-trimethyl-4-(2-chlorophenyl)-1H-pyrazolo[3,4-b]pyridin-5-carboxylic acid ethyl ester, hydrochloride.

Starting from 1,3-dimethyl-5-pyrazolamine and ethyl-2-(2-chlorobenzyliden)acetoacetate. M.p. 240°–242° C.

EXAMPLE 8

4,7-dihydro-1,3,6-trimethyl-4-(3-nitrophenyl)-1H-pyrazolo[3,4-b]pyridin-5-carboxylic acid ethyl ester, hydrochloride.

Starting from 1,3-dimethyl-5-pyrazolamine and ethyl-2-(3-nitrobenzyliden)acetoacetate. M.p. 237° C. (dec.).

EXAMPLE 9

4,7-dihydro-1,3,6-trimethyl-4-(2-nitrophenyl)-1H-pyrazolo[3,4-b]pyridin-5-carboxylic acid 2-methoxyethyl ester, hydrochloride.

Starting from 1,3-dimethyl-5-pyrazolamine and 2-methoxyethyl-2-(2-nitrobenzyliden)acetoacetate. M.p. 170°–174° C.

EXAMPLE 10

1-Ethyl-4,7-dihydro-3,6-dimethyl-4-(2-nitrophenyl)-1H-pyrazolo[3,4-b]pyridin-5-carboxylic acid methyl ester, hydrochloride. M.p. 230°–232° C.

Starting from 3-ethyl-1-methyl-5-pyrazolamine and methyl-2-(2-nitrobenzyliden)acetoacetate.

The reflux is preferably carried out under nitrogen stream.

Essentially following the procedure outlined in the above examples, the following compounds or the corresponding acid addition salts can be prepared:

4,7-dihydro-1,3,6-trimethyl-4-(pentafluorophenyl)-1H-pyrazolo[3,4-b]pyridin-5-carboxylic acid (1,1-dimethyl)ethyl ester 4,7-dihydro-1,3,6-trimethyl-4-(2-nitrophenyl)-1H-pyrazolo[3,4-b]pyridin-5-carboxylic acid (1,1-dimethyl)ethyl ester 4,7-dihydro-1,3,6-trimethyl-4-(3-fluorophenyl)-1H-pyrazolo[3,4-b]pyridin-5-carboxylic acid ethyl ester 4,7-dihydro-1,3,6-trimethyl-4-(2,3-dichlorophenyl)-1H-pyrazolo[3,4-b]pyridin-5-carboxylic acid propyl ester 4,7-dihydro-1,3,6-trimethyl-4-(2,3-chlorofluorophenyl)-1H-pyrazolo[3,4-b]pyridin-5-carboxylic acid n-butyl ester 4,7-dihydro-1,3,6-trimethyl-4-(2-ethylphenyl)-1H-pyrazolo[3,4-b]pyridin-5-carboxylic acid n-pentyl ester 4,7-dihydro-1,3,6-trimethyl-4-(2,3-dimethylphenyl)-1H-pyrazolo[3,4-b]pyridin-5-carboxylic acid n-hexyl ester 4,7-dihydro-1,3,6-trimethyl-4-(2,6-dimethylphenyl)-1H-pyrazolo[3,4-b]pyridin-5-carboxylic acid n-hexyl ester 4,7-dihydro-1,3,6-trimethyl-4-(2-isopropylphenyl)-1H-pyrazolo[3,4-b]pyridin-5-carboxylic acid sec-butyl ester 4,7-dihydro-1,3,6-trimethyl-4-(2-trifluoromethylphenyl)-1H-pyrazolo[3,4-b]pyridin-5-carboxylic acid methyl ester 4,7-dihydro-1,3,6-trimethyl-4-(3-trifluoromethylphenyl)-1H-pyrazolo[3,4-b]pyridin-5-carboxylic acid methyl ester 4,7-dihydro-1,3,6-trimethyl-4-(2-methoxycarbonylphenyl)-1H-pyrazolo[3,4-b]acid methyl ester 4,7-dihydro-1,3,6-trimethyl-4-(2-ethoxyphenyl)-1H-pyrazolo[3,4-b]pyridin-5-carboxylic acid i-propyl ester 4,7-dihydro-1,3,6-trimethyl-4-(2,6-dichlorophenyl)-1H-pyrazolo[3,4-b]pyridin-5-carboxylic acid i-propyl ester 4,7-dihydro-1,3,6-trimethyl-4-(2,3-dimethoxyphenyl)-1H-pyrazolo[3,4-b]pyridin-5-carboxylic acid methyl ester.

EXAMPLE 11

4,7-dihydro-1,6-dimethyl-3-phenyl-4-(2-methylphenyl)-1H-pyrazolo[3,4-b]pyridin-5-carboxylic acid ethyl ester, hydrochloride.

Ethyl-2-(2-methylbenzyliden)acetoacetate (0.050 mol) is added to 1-methyl-3-phenyl-5-pyrazolamine (0.050 mol) in ethanol (50 ml) and refluxed for 90 minutes. The mixture is then cooled to room temperature, further ethyl-2-(2-methylbenzyliden)acetoacetate (0.050 mol) is added thereto, and the mixture refluxed for further 90 minutes. The reaction mixture is then cooled, the solvent is evaporated, and the residue is taken up in ethyl ether, collected by filtration, and dried. The product is dissolved in methanol and a mixture of hydrochloric acid and methanol (45 mmol of HCl) is added thereto. The product of the title precipitates by adding ethyl ether. M.p. 187° C. (dec.).

Essentially following the procedure of the above example the following compounds are obtained, starting from the suitable reactants:

EXAMPLE 12

4,7-dihydro-1,6-dimethyl-3-phenyl-4-(3-methoxyphenyl)-1H-pyrazolo[3,4-b]pyridin-5-carboxylic acid ethyl ester, hydrochloride.

Starting from 1-methyl-3-phenyl-5-pyrazolamine and ethyl-2-(3-methoxybenzyliden)acetoacetate. M.p. 200°–204° C.

EXAMPLE 13

4,7-dihydro-1,6-dimethyl-3-phenyl-4-(2-nitrophenyl)-1H-pyrazolo[3,4-b]pyridin-5-carboxylic acid ethyl ester, hydrochloride.

Starting from 1-methyl-3-phenyl-5-pyrazolamine and ethyl-2-(2-nitrobenzyliden)acetoacetate. M.p. 175° C. (dec.).

EXAMPLE 14

4,7-dihydro-1,6-dimethyl-3-phenyl-4-(2-nitrophenyl)-1H-pyrazolo[3,4-b]pyridin-5-carboxylic acid isopropyl ester, hydrochloride.

Starting from 1-methyl-3-phenyl-5-pyrazolamine and isopropyl-2-(2-nitrobenzyliden)acetoacetate. M.p. 162°–167° C. (dec.).

EXAMPLE 15

4,7-dihydro-1,6-dimethyl-3-phenyl-4-(3-nitrophenyl)-1H-pyrazolo[3,4-b]pyridin-5-carboxylic acid ethyl ester, hydrochloride.

Starting from 1-methyl-3-phenyl-5-pyrazolamine and ethyl-2-(3-nitrobenzyliden)acetoacetate. M.p. 212°–215° C. (dec.).

EXAMPLE 16

4,7-dihydro-1,6-dimethyl-3-phenyl-4-(2-nitrophenyl)-1H-pyrazolo[3,4-b]pyridin-5-carboxylic acid 2-methoxyethyl ester, hydrochloride.

Starting from 1-methyl-3-phenyl-5-pyrazolamine and 2-methoxyethyl-2-(2-nitrobenzilyden)acetoacetate. M.p. 167°–174° C.

EXAMPLE 17

4,7-dihydro-1,6-dimethyl-4-(2,5-dimethylphenyl)-3-phenyl-1H-pyrazolo[3,4-b]pyridin-5-carboxylic acid ethyl ester, hydrochloride. M.p. 184°–189° C.

Starting from 1-methyl-3-phenyl-5-pyrazolamine and ethyl-2-(2,5-dimethylbenzyliden)acetoacetate in equimolar proportions. The crude reaction product is taken up with ethyl ether, washed with 2% $H_2SO_4$, water, and then 5% $NaHCO_3$ until neutralization of the mother liquors. After drying over $Na_2SO_4$ the hydrochloride of the title compound is obtained by reacting with HCl/ethyl ether. Crystallization from isopropanol/ethyl ether.

EXAMPLE 18

4,7-Dihydro-1,6-dimethyl-4-(2-nitrophenyl)-3-phenyl-1H-pyrazolo[3,4-b]pyridin-5-carboxylic acid methyl ester, hydrochloride. M.p. 145°–148° C.

1-Methyl-3-phenyl-5-pyrazolamine (3,46 g; 0.02 mol), 2-nitrobenzaldehyde (3,02 g; 0.02 mol), and methyl acetoacetate (2,32 g; 0.02 mol) are refluxed in isopropanol (30 ml) under nitrogen stream and in the dark. Reflux is continued for about 12 hours. After cooling to room temperature, the solvent is stripped off, the dry residue is taken up with ethyl ether, washed with 2% $H_2SO_4$, water, and then $NaHCO_3$. After drying over $MgSO_4$, the solvent is stripped off and the residue is taken up with methanol and salified as usual using 20% HCl/ethanol.

EXAMPLE 19

4,7-Dihydro-6-methyl-4-(2-nitrophenyl)-3-phenyl-1H-pyrazolo[3,4-b]pyridin-5-carboxylic acid ethyl ester. M.p. 185°–187° C. (methanol).

Starting from 3-phenyl-5-(1H)pyrazolamine and ethyl-2-(2-nitrobenzyliden) acetoacetate. The reflux is carried out under nitrogen stream and in the dark.

EXAMPLE 20

4,7-Dihydro-4-(2,5-dimethylphenyl)-6-methyl-3-phenyl-1H-pyrazolo[3,4-b]pyridin-5-carboxylic acid ethyl ester. M.p. 270°–273° C. (ethanol).

Starting from 3-phenyl-5-(1H)pyrazolamine and ethyl-2-(2,5-dimethylbenzyliden)acetoacetate.

EXAMPLE 21

4,7-dihydro-6-methyl-1,3-diphenyl-4-(3-nitrophenyl)-1H-pyrazolo[3,4-b]pyridin-5-carboxylic acid methyl ester.

Methyl-2-(3-nitrobenzyliden)acetoacetate is added to 1,3-diphenyl-5-pyrazolamine (0.010 mol) in ethanol (16 ml) and refluxed for 90 minutes under nitrogen. After cooling to room temperature, the solvent is evaporated under reduced pressure, the residue is taken up in ethyl ether, discarding the insolubles, and then the solvent is evaporated. Upon crystallization from methanol, the product of the title is obtained. M.p. 186°–189° C.

EXAMPLE 22

4,7-dihydro-6-methyl-3-phenyl-4-(3-nitrophenyl)-1H-pyrazolo[3,4-b]pyridin-5-carboxylic acid methyl ester.

3-Phenyl-5-pyrazolamine (5 m mol) is dissolved in ethanol (12 ml) methyl-2-(3-nitrobenzyliden)acetoacetate is added thereto, and refluxed for 3 hours, under nitrogen stream. The reaction mixture is then cooled to room temperature, the solvent is evaporated under reduced pressure, and the residue is taken up in methylene chloride. The product is purified by silica gel column chromatography, eluting with methylene chloride/methanol, 99:1. The solvent is then evaporated from the collected fractions, and the residue is crystallized from ethyl acetate/n-hexane to give the product of the title. M.p. 240°–241° C.

Essentially following the above procedures, the following compounds or the corresponding acid addition salts can be prepared:

4,7-dihydro-6-methyl-3-phenyl-4-(pentafluorophenyl)-1H-pyrazolo[3,4-b]pyridin-5-carboxylic acid (1,1-dimethyl)ethyl ester 4,7-dihydro-6-methyl-3-phenyl-4-(2-methylphenyl)-1H-pyrazolo[3,4-b]pyridin-5-carboxylic acid (1,1-dimethyl)ethyl ester 4,7-dihydro-6-methyl-3-phenyl-4-(2-nitrophenyl)-1H-pyrazolo[3,4-b]pyridin-5-carboxylic acid (1,1-dimethyl)ethyl ester 4,7-dihydro-6-methyl-3-phenyl-4-(3,4-dichlorophenyl)-1H-pyrazolo[3,4-b]pyridin-5-carboxylic acid ethyl ester 4,7-dihydro-6-methyl-3-phenyl-4-(3-fluorophenyl)-1H-pyrazolo[3,4-b]pyridin-5-carboxylic acid ethyl ester 4,7-dihydro-6-methyl-3-phenyl-4-(2,3-dichlorophenyl)-1H-pyrazolo[3,4-b]pyridin-5-carboxylic acid propyl ester 4,7-dihydro-6-methyl-3-phenyl-4-(2,3-chlorofluorophenyl)-1H-pyrazolo[3,4-b]pyridin-5-carboxylic acid n-butyl ester 4,7-dihydro-6-methyl-3-phenyl-4-(2-ethylphenyl)-1H-pyrazolo[3,4-b]pyridin-5-carboxylic acid n-pentyl ester 4,7-dihydro-6-methyl-3-phenyl-4-(2,3-dimethylphenyl)-1H-pyrazolo[3,4-b]pyridin-5-carboxylic acid n-hexyl ester 4,7-dihydro-6-methyl-3-phenyl-4-(2-(1-methylethyl)phenyl)-1H-pyrazolo[3,4-b]pyridin-5-carboxylic acid sec-butyl ester 4,7-dihydro-6-methyl-3-phenyl-4-(3-trifluoromethylphenyl)-1H-pyrazolo[3,4-b]pyridin-5-carboxylic acid methyl ester 4,7-dihydro-6-methyl-3-phenyl-4-(2-methoxycarbonylphenyl)-1H-pyrazolo[3,4-b]pyridin-5-carboxylic acid methyl ester 4,7-dihydro-6-methyl-3-phenyl-4-(2-ethoxyphenyl)-1H-pyrazolo[3,4-b]pyridin-5-carboxylic acid i-propyl ester 4,7-dihydro-6-methyl-3-phenyl-4-(2,3-dimethoxyphenyl)-1H-pyrazolo[3,4-b]pyridin-5-carboxylic acid methyl ester

EXAMPLE 23

3-Ethyl-4,7-dihydro-1,6-dimethyl-4-(2-nitrophenyl)-1H-pyrazolo[3,4-b]pyridin-5-carboxylic acid ethyl ester, hydrochloride. M.p. 243°–247° C. (Dec.) (ethanol)

Starting from 3-ethyl-1-methyl-5-pyrazolamine and ethyl-2-(2-nitrobenzyliden)acetoacetate.

EXAMPLE 24

3-Ethyl-4,7-dihydro-1,6-dimethyl-4-(2-nitrophenyl)-1H-pyrazolo[3,4-b]pyridin-5-carboxylic acid, 2-methoxy ethyl ester. M.p. 172°–176° C. (ethyl ether)

Starting from 3-ethyl-1-methyl-5-pyrazolamine and (2-methoxyethyl-2-(2-nitrobenzyliden)acetoacetate.

Essentially following the procedures outlined in the above examples, the following compounds or the corresponding acid addition salts can be prepared:

4,7-dihydro-1,6-dimethyl-3-ehtyl-4-(pentafluorophenyl)-1H-pyrazolo[3,4-b]pyridin-5-carboxylic acid (1,1-dimethyl)ethyl ester 4,7-dihydro-1,6-dimethyl-3-ethyl-4-(2-nitrophenyl)-1H-pyrazolo[3,4-b]pyridin-5-carboxylic acid (1,1-dimethyl)ethyl ester 4,7-dihydro-1,6-dimethyl-3-ethyl-4-(3,4-dichlorophenyl)-1H-pyrazolo[3,4-b]pyridin-5-carboxylic acid ethyl ester 4,7-dihydro-1,6-dimethyl-3-ethyl-4-(3-fluorophenyl)-1H-pyrazolo[3,4-b]pyridin-5-carboxylic acid ethyl ester 4,7-dihydro-1,6-dimethyl-3-ethyl-4-(2,3-dichlorophenyl)-1H-pyrazolo[3,4-b]pyridin-5-carboxylic acid propyl ester 4,7-dihydro-1,6-dimethyl-3-ethyl-4-(2,3-chlorofluorophenyl)-1H-pyrazolo[3,4-b]pyridin-5-carboxylic acid n-butyl ester 4,7-dihydro-1,6-dimethyl-3-ethyl-4-(2-ethylphenyl)-1H-pyrazolo[3,4-b]pyridin-5-carboxylic acid n-pentyl ester 4,7-dihydro-1,6-dimethyl-3-ethyl-4-(2,3-dimethylphenyl)-1H-pyrazolo[3,4-b]pyridin-5-carboxylic acid n-hexyl ester 4,7-dihydro-1,6-dimethyl-3-ethyl-4-(2-(1-methylethyl)phenyl)-1H-pyrazdo[3,4-b]pyridin-5-carboxylic acid sec-butyl ester 4,7-dihydro-1,6-dimethyl-3-ethyl-4-(3-trifluoromethylphenyl)-1H-pyrazolo[3,4-b]pyridin-5-carboxylic acid methyl ester 4,7-dihydro-1,6-dimethyl-3-ethyl-4-(2-methoxycarbonylphenyl)-1H-pyrazolo[3,4-b]pyridin-5-carboxylic acid methyl ester 4,7-dihydro-1,6-dimethyl-3-ethyl-4-(2-ethoxyphenyl)-1H-pyrazolo[3,4-b]pyridin-5-carboxylic acid i-propyl ester 4,7-dihydro-1,6-dimethyl-3-ethyl-4-(2,3-dimethoxyphenyl)-1H-pyrazolo[3,4-b]pyridin-5-carboxylic acid methyl ester

EXAMPLE 25

4,7-Dihydro-1,6-dimethyl-4-(3-nitrophenyl)-3-propyl-1H-pyrazolo[3,4-b]pyridin-5-carboxylic acid methyl ester, hydrochloride. M.p. 240° C. (methanol)

Starting from 3-propyl-1-methyl-5-pyrazolamine and methyl-2-(3-nitrobenzyliden)acetoacetate.

EXAMPLE 26

4,7-Dihydro-1,6-dimethyl-4-(2-nitrophenyl)-3-propyl-1H-pyrazolo[3,4-b]pyridin-5-carboxylic acid methyl ester. M.p. 175°–186° C.

Starting from 3-propyl-1-methyl-5-pyrazolamine and methyl-2-(2-nitrobenzyliden)acetoacetate. Essentially following the procedures outlined in the above examples, the following compounds or the corresponding acid addition salts can be prepared:

4,7-dihydro-1,6-dimethyl-3-propanyl-4-(pentafluorophenyl)-1H-pyrazolo[3,4-b]pyridin-5-carboxylic acid (1,1-dimethyl)ethyl ester 4,7-dihydro-1,6-dimethyl-3-propanyl-4-(2-nitrophenyl)-1H-pyrazolo[3,4-b]pyridin-5-carboxylic acid (1,1-dimethyl)ethyl ester 4,7-dihydro-1,6-dimethyl-3-propanyl-4-(3,4-dichlorophenyl)-1H-pyrazolo[3,4-b]pyridin-5-carboxylic acid ethyl ester 4,7-dihydro-1,6-dimethyl-3-propanyl-4-(3-fluorophenyl)-1H-pyrazolo[3,4-b]pyridin-5-carboxylic acid ethyl ester 4,7-dihydro-1,6-dimethyl-3-propanyl-4-(2,3-dichlorophenyl)-1H-pyrazolo[3,4-b]pyridin-5-carboxylic acid propyl ester 4,7-dihydro-1,6-dimethyl-3-propanyl-4-(2,3-chlorofluorophenyl)-1H-pyrazolo[3,4-b]pyridin-5-carboxylic acid n-butyl ester 4,7-dihydro-1,6-dimethyl-3-propanyl-4-(2-ethylphenyl)-1H-pyrazolo[3,4-b]pyridin-5-carboxylic acid n-pentyl ester 4,7-dihydro-1,6-dimethyl-3-propanyl-4-(2,3-dimethylphenyl)-1H-pyrazolo[3,4-b]pyridin-5-carboxylic acid n-hexyl ester 4,7-dihydro-1,6-dimethyl-3-propanyl-4-(2-(1-methylethyl)phenyl)-1H-pyrazolo[3,4-b]pyridin-5-carboxylic acid sec-butyl ester 4,7-dihydro-1,6-dimethyl-3-propanyl-4-(3-trifluoromethylphenyl)-1H-pyrazolo[3,4-b]pyridin-5-carboxylic acid methyl ester 4,7-dihydro-1,6-dimethyl-3-propanyl-4-(2-methoxycarbonylphenyl)-1H-pyrazolo[3,4-b]pyridin-5-carboxylic acid methyl ester 4,7-dihydro-1,6-dimethyl-3-propanyl-4-(2-ethoxyphenyl)-1H-pyrazolo[3,4-b]pyridin-5-carboxylic acid i-propyl ester 4,7-dihydro-1,6-dimethyl-3-propanyl-4-(2,3-dimethoxyphenyl)-1H-pyrazolo[3,4-b]pyridin-5-carboxylic acid methyl ester Essentially following the procedure described in Example 4, the following compounds are obtained:

EXAMPLE 27

4,7-dihydro-1,6-dimethyl-3-(1-methylethyl)-4-(2-nitrophenyl)-1H-pyrazolo[3,4-b]pyridin-5-carboxylic acid ethyl ester, hydrochloride.

Starting from 1-methyl-3-(1-methylethyl)-5-pyrazolamine and ethyl-2-(2-nitrobenzyliden)acetoacetate. M.p. 218° C. (Dec.).

EXAMPLE 28

4,7-dihydro-1,6-dimethyl-3-(1-methylethyl)-4-(2-nitrophenyl)-1H-pyrazolo[3,4-b]pyridin-5-carboxylic acid (1-methylethyl) ester, hydrochloride.

Starting from 1-methyl-3-(1-methylethyl)-5-pyrazolamine and (1-methylethyl)-2-(2-nitrobenzyliden)acetoacetate. M.p. 229°–231° C. (Dec.).

EXAMPLE 29

4,7-Dihydro-1,6-dimethyl-3-(1-methylethyl)-4-(2-nitrophenyl)-1H-pyrazolo[3,4-b]pyridin-5-carboxylic acid 2-methoxyethyl ester, hydrochloride.

Starting from 1-methyl-3-(1-methylethyl)-5-pyrazolamine and 2-methoxyethyl-2-(2-nitrobenzyliden)acetoacetate. M.p. 119°–124° C. (Dec.).

EXAMPLE 30

4,7-dihydro-1,6-dimethyl-3-(1-methylethyl)-4-(2-methylphenyl)-1H-pyrazolo[3,4-b]pyridin-5-carboxylic acid ethyl ester, hydrochloride.

Starting from 1-methyl-3-(1-methylethyl)-5-pyrazolamine and ethyl-2-(2-methylbenzyliden)acetoacetate. M.p. 226°–231° C.

EXAMPLE 31

4,7-dihydro-1,6-dimethyl-3-(1-methylethyl)-4-(3-trifluoromethylphenyl)-1H-pyrazolo[3,4-b]-pyridin-5-carboxylic acid ethyl ester, hydrochloride.

Starting from 1-methyl-3-(1-methylethyl)-5-pyrazolamine and ethyl-2-(3-trifluoromethylbenzyliden)acetoacetate. M.p. 255°–260° C. (dec.).

EXAMPLE 32

4,7-Dihydro-1,6-dimethyl-3-(1-methylethyl)-3-nitrophenyl-1H-pyrazolo[3,4-b]pyridin-5-carboxylic acid 2-[(phenylmethyl)methylamino]ethyl ester, dihydrochloride. M.p. 220°–228° C.

3-Nitrobenzaldehyde (3,02 g; 0.02 mol), acetoacetic acid 2-[(phenylmethyl)methylamino]ethyl ester (5,0 g; 0.02 mol), 1-methyl-3-(1-methylethyl)-5-pyrazolamine in propanol (40 ml) are refluxed under nitrogen stream and in the dark for about 8 hours.

The crude reaction product is worked up essentially as in Example 29 but using n-hexane/ethanol 8:2 as the eluent in the flash chromatography.

EXAMPLE 33

4,7-Dihydro-1,6-dimethyl-4-(2,5-dimethylphenyl)-3-(1-methylethyl)-1H-pyrazolo[3,4-b]pyridin-5-carboxylic acid ethyl ester, hydrochloride. M.p. 204°–211° C.

Starting from 3-(1-methylethyl)-1-methyl-5-pyrazolamine and ethyl-2-(2,5-dimethylbenzyliden)acetoacetate.

EXAMPLE 34

4,7-Dihydro-1,6-dimethyl-3-(1-methylethyl)-4-(1-naphthyl)-1H-pyrazolo[3,4-b]pyridin-5-carboxylic acid methyl ester, hydrochloride. M.p. 239°–241° C. (methanol)

Starting from 3-(1-methylethyl)-1-methyl-5-pyrazolamine and methyl-2-(1-naphthyliden)acetoacetate in equimolar proportions.

The crude reaction product is dissolved in ethyl acetate, washed sequentially with 2% $H_2SO_4$ and water, dried over $Na_2SO_4$, dissolved in ethyl ether and salified by bubbling hydrogen chloride into the solution.

EXAMPLE 35

4,7-Dihydro-1,6-dimethyl-3-(1-methylethyl)-4-(2-nitrophenyl)-1H-pyrazolo[3,4-b]pyridin-5-carboxylic acid methyl ester, hydrochloride. M.p. 222°–228° C.

Starting from 1-methyl-3-(1-methylethyl)-5-pyrazolamine (2,79 g; 0.02 mol), 2-nitrobenzaldehyde (3,02 g; 0.02 mol) and methyl acetoacetate (2,32 g; 0.02 mol), in propanol (30 ml). The mixture is refluxed for about 8 hours under nitrogen stream and in the dark and then worked up as usual.

EXAMPLE 36

4,7-Dihydro-1,6-dimethyl-3-(1-methylethyl)-4-[2-(trifluoromethyl)phenyl]-1H-pyrazolo[3,4-b]pyridin-5-carboxylic acid ethyl ester, hydrochloride. M.p. 197°–199° C. (isopropanol/ethyl ether)

Starting from 1-methyl-3-(1-methylethyl)-5-pyrazolamine and ethyl-2[(2-trifluoromethyl)benzyliden]acetoacetate in equimolar proportion.

EXAMPLE 37

4-(2-Fluorophenyl)-4,7-dihydro-1,6-dimethyl-3-(1-methylethyl)-1H-pyrazolo[3,4-b]pyridin-5-carboxylic acid ethyl ester, hydrochloride. M.p. 210°–217° C. (Dec.)

Starting from 1-methyl-3-(1-methylethyl)-5-pyrazolamine (2,78 g; 0.02 mol), 2-fluorobenzaldehyde (2,48 g; 0.02 mol) and ethyl acetoacetate (2,6 g; 0.02 mol) in isopropanol (30 ml).

The mixture is refluxed for about 8 hours. The apparatus is protected from air and light as usual and the work up procedure is not dissimilar from those above described.

EXAMPLE 38

4-Pentafluorophenyl-4,7-dihydro-1,6-dimethyl-3-(1-methylethyl)-1H-pyrazolo[3,4-b]pyridin-5-carboxylic acid ethyl ester, hydrochloride. M.p. 219°–222° C.

Starting from 1-methyl-3-(1-methylethyl)-5-pyrazolamine and ethyl-2-(pentafluorobenzyliden)acetoacetate in equimolar proportions.

EXAMPLE 39

4,7-Dihydro-1,6-dimethyl-3-(1-methylethyl)-4-(3-nitrophenyl)-1H-pyrazolo[3,4-b]pyridin-5-carboxylic acid methyl ester, hydrochloride. M.p. 248°–250° C.

Starting from 1-methyl-3-(1-methylethyl)-5-pyrazolamine and methyl-2-(3-nitrobenzyliden)acetoacetate in equimolar proportions. The mixture is refluxed in ethanol for about 6 hours, extracted with ethylacetoacetate and worked up as usual.

EXAMPLE 40

4,7-Dihydro-1,6-dimethyl-3-(1-methylethyl)-4-(3-nitrophenyl)-1H-pyrazolo[3,4-b]pyridin-5-carboxylic acid ethyl ester, hydrochloride. M.p. 249°-253° C. (methanol)

Starting from 1-methyl-3-(1-methylethyl)-5-pyrazolamine (0.02 mol), 3-nitrobenzaldehyde (0.02 mol) and ethyl acetoacetate (0.02 mol).

EXAMPLE 41

4,7-Dihydro-1,6-dimethyl-3-(2-methylpropyl)-4-(2-nitro phenyl)-1H-pyrazolo[3,4-b]pyridin-5-carboxylic methyl ester, hydrochloride. M.p. 160°-167° C. (isopropanol/ethyl ether)

1-methyl-3-(2-methylpropyl)-5-pyrazolamine (0.015 mol) methyl-2-(2-nitrobenzyliden)acetoacetate (0.015 mol) in absolute ethanol are refluxed for about 24 hours. Then the solvent is evaporated under vacuum and the residue is dissolved in ethyl acetate and reacted with a molar equivalent of 15% HCl/ethyl ether.

After washing with water and drying, the ethereal phase is evaporated under vacuum leaving the crude product which is purified by flash chromatography and salified as usual.

EXAMPLE 42

4,7-Dihydro-1,6-dimethyl-3-(2-methylpropyl)-4-(3-nitro phenyl)-1H-pyrazolo[3,4-b]pyridin-5-carboxylic acid methyl ester, hydrochloride. M.p. 168°-172° C.

Starting from 1-methyl-3-(2-methylpropyl)-5-pyrazolamine and methyl-2-(2-nitrobenzyliden)acetoacetate.

EXAMPLE 43

4,7-Dihydro-1,6-dimethyl-3-(2-methylpropyl)-4-(2-nitrophenyl)-1H-pyrazolo[3,4-b]pyridin-5-carboxylic acid 2-methoxyethyl ester. M.p. 186°-189° C. (Dec.)

Starting from 1-methyl-3-(2-methylpropyl)-5-pyrazolamine and 2-methoxyethyl-2-(2-nitrobenzyliden)acetoacetate.

EXAMPLE 44

4,7-Dihydro-1,6-dimethyl-3-(2-methylpropyl)-4-(2-nitro phenyl)-1H-pyrazolo[3,4-b]pyridin-5-carboxylic acid ethyl ester, hydrochloride. M.p. 158°-161° C. (isopropanol/ethyl ether)

Starting from 1-methyl-3-(2-methylpropyl)-5-pyrazolamine and ethyl 2-(2-nitrobenzyliden)acetoacetate.

EXAMPLE 45

3-Butyl-4,7-dihydro-1,6-dimethyl-4-(3-nitrophenyl)-1H-pyrazolo[3,4-b]pyridin-5-carboxylic acid 2-methoxyethyl ester, hydrochloride. M.p. 200° Dec. (methanol/ethyl ether)

Starting from 3-butyl-1-methyl-5-pyrazolamine and (2-methoxyethyl)-2-(3-nitrobenzyliden)acetoacetate in equimolar proportions, in isopropanol.

EXAMPLE 46

3-Butyl-4,7-dihydro-1,6-dimethyl-4-(3-nitrophenyl)-1H-pyrazolo[3,4-b]pyridin-5-carboxylic acid methyl ester, hydrochloride. M.p. 215°-230° C. (methanol)

Starting from 3-butyl-1-methyl-5-pyrazolamine and methyl-2-(3-nitrobenzyliden)acetoacetate in equimolar proportions, in isopropanol. After refluxing for about 8 hours the reaction mixture is worked up as usual.

EXAMPLE 47

3-Butyl-4,7-dihydro-1,6-dimethyl-4-(2-nitrophenyl)-1H-pyrazolo[3,4-b]pyridine 5-carboxylic acid 2-methoxyethyl ester. M.p. 131°-139° C. (ethyl ether)

Starting from 3-butyl-1-methyl-5-pyrazolamine and (2-methoxyethyl)-2-(2-nitrobenzyliden)acetoacetate.

EXAMPLE 48

3-Butyl-4,7-dihydro-1,6-dimethyl-4-(2-nitrophenyl)-1H-pyrazolo[3,4-b]pyridin-5-carboxylic acid methyl ester. M.p. 191°-201° C. (ethyl ether)

Starting from 3-butyl-1-methyl-5-pyrazolamine and methyl-2-(2-nitrobenzyliden)acetoacetate in equimolar proportions.

Essentially following the procedures outlined in the above examples, the following compounds or the corresponding acid addition salts can be prepared:

4,7-dihydro-1,6-dimethyl-3-(1,1-dimethyl)ethyl-4-(pentafluorophenyl)-1H-pyrazolo[3,4-b]pyridin-5-carboxylic acid (1,1-dimethyl)ethyl ester 4,7-dihydro-1,6-dimethyl-3-(1,1-dimethyl)ethyl-4-(3-nitrophenyl)-1H-pyrazolo[3,4-b]pyridin-5-carboxylic acid (1,1-dimethyl)ethyl ester 4,7-dihydro-1,6-dimethyl-3-(1,1-dimethyl)ethyl-4-(3,4-dichlorophenyl)-1H-pyrazolo[3,4-b]pyridin-5-carboxylic acid ethyl ester 4,7-dihydro-1,6-dimethyl-3-(1,1-dimethyl)ethyl-4-(3-fluorophenyl)-1H-pyrazolo[3,4-b]pyridin-5-carboxylic acid ethyl ester 4,7-dihydro-1,6-dimethyl-3-(1,1-dimethyl)ethyl-4-(2,3-dichlorophenyl)-1H-pyrazolo[3,4-b]pyridin-5-carboxylic acid propyl ester 4,7-dihydro-1,6-dimethyl-3-(1,1-dimethyl)ethyl-4-(2,3-chlorofluorophenyl)-1H-pyrazolo[3,4-b]pyridin-5-carboxylic acid n-butyl ester 4,7-dihydro-1,6-dimethyl-3-(1,1-dimethyl)ethyl-4-(2-ethylphenyl)-1H-pyrazolo[3,4-b]pyridin-5-carboxylic acid n-pentyl ester 4,7-dihydro-1,6-dimethyl-3-(1,1-dimethyl)ethyl-4-(2,3-dimethylphenyl)-1H-pyrazolo[3,4-b]pyridin-5-carboxylic acid n-hexyl ester 4,7-dihydro-1,6-dimethyl-3-(1,1-dimethyl)ethyl-4-(2-(1-methylethyl)phenyl)-1H-pyrazolo[3,4-b]pyridin-5-carboxylic acid sec-butyl ester 4,7-dihydro-1,6-dimethyl-3-(1,1-dimethyl)ethyl-4-(3-trifluoromethylphenyl)-1H-pyrazolo[3,4-b]pyridin-5-carboxylic acid methyl ester 4,7-dihydro-1,6-dimethyl-3-(1,1-dimethyl)ethyl-4-(2-methoxycarbonylphenyl)-1H-pyrazolo[3,4-b]pyridin-5-carboxylic acid methyl ester 4,7-dihydro-1,6-dimethyl-3-(1,1-dimethyl)ethyl-4-(2-ethoxyphenyl)-1H-pyrazolo[3,4-b]pyridin-5-carboxylic acid i-propyl ester 4,7-dihydro-1,6-dimethyl-3-(1,1-dimethyl)ethyl-4-(2,3-dimethoxyphenyl)-1H-pyrazolo[3,4-b]pyridin-5-carboxylic acid methyl ester

EXAMPLE 49

4,7-Dihydro-1,6-dimethyl-3-(1,1-dimethylethyl)-4-(2-nitro phenyl)-1H-pyrazolo[3,4-b]pyridin-5-carboxylic acid methyl ester, hydrochloride. M.P. 163°-172° C. (Dec.) (ethanol/ethyl ether)

Reflux under nitrogen stream and possibly purify the oily free base by flash chromatography using 350 ml of silica gel and CHCl$_3$/CH$_3$OH, 95:5 as the eluent, before salifying as usual.

EXAMPLE 50

4,7-Dihydro-1,6-dimethyl-3-(1,1-dimethylethyl)-4-(2-nitro phenyl)-1H-pyrazolo[3,4-b]pyridin-5-carboxylic acid 2-methoxyethyl ester, hydrochloride. M.p. 118°-160° C. (Dec.)

Work up as in Example 49.

EXAMPLE 51

4,7-Dihydro-1,6-dimethyl-3-(1,1-dimethylethyl)-4-(2-nitrophenyl)-1H-pyrazolo[3,4-b]pyridin-5-carboxylic ethyl ester, hydrochloride. M.p. 140°-160° C. (Dec.)

Work up as in Example 49.

EXAMPLE 52

4,7-Dihydro-1,6-dimethyl-3-(1,1-dimethylethyl)-4-(3-nitrophenyl)-1H-pyrazolo[3,4-b]pyridin-5-carboxylic acid methyl ester, hydrochloride. M.p. 230°-233° C. (Dec.) (isopropanol)

The crude reaction product is dissolved in ethyl acetate, washed with 2% HCl, water, dried over Na$_2$SO$_4$, dissolved in isopropanol and salified as usual.

EXAMPLE 53

3-Cyclohexyl-4,7-dihydro-1,6-dimethyl-4-(3-nitrophenyl)-1H-pyrazolo[3,4-b]pyridin-5-carboxylic acid methyl ester. M.p. 235°-245° C. (Dec.) (ethanol/methanol)

Starting from 3-cyclohexyl-1-methyl-5-pyrazolamine and methyl-2-(3-nitrobenzyliden)acetoacetate in equimolar proportions.

EXAMPLE 54

3-Cyclohexyl-4,7-dihydro-1,6-dimethyl-4-(2-nitrophenyl)-1H-pyrazolo[3,4-b]pyridin-5-carboxylic acid methyl ester, hydrochloride. M.p. 219°-228° C. (isopropanol/ethyl ether)

Starting from 3-cyclohexyl-1-methyl-5-pyrazolamine and methyl-2-(2-nitrobenzyliden)acetoacetate in equimolar proportions, in absolute ethanol.

The mixture is refluxed for about 24 hours using the usual precautions (in the dark, under nitrogen stream), the solvent is stripped off and the residue is dissolved in ethyl acetate. The solvent is washed with 1% HCl and water, dried, and evaporated to dryness. The crude residue is purified by flash chromatography. After dissolving the obtained product in ethyl ether/isopropanol, dihydrogen chloride in ethyl ether is added thereto and the obtained solid is collected and crystallized from isopropanol/ether.

EXAMPLE 55

3-Cyclohexyl-4,7-dihydro-1,6-dimethyl-4-(2-nitrophenyl)-1H-pyrazolo[3,4-b]pyridin-5-carboxylic acid 2-methoxyethyl ester. M.p. 203°-207° C.

Starting from 3-cyclohexyl-1-methyl-5-pyrazolamine and 2-methoxyethyl-2-(2-nitrobenzyliden)acetoacetate in about equimolar proportions.

EXAMPLE 56

3-Cyclohexyl-4,7-dihydro-1,6-dimethyl-4-(2-nitrophenyl)-1H-pyrazolo[3,4-b]pyridin-5-carboxylic acid ethyl ester, hydrochloride. M.p. 160°-165° C. (Dec.)

Starting from 3-cyclohexyl-1-methyl-5-pyrazolamine and 2-methyl-2-(2-nitrobenzyliden) acetoacetate in about equimolar proportions. Work up as usual.

EXAMPLE 57

"One pot" preparation of 4,7-dihydro-1,6-dimethyl-3-phenyl-4-(3-nitrophenyl)-1H-pyrazolo[3,4-b]pyridin-5-carboxylic acid ethyl ester, hydrochloride. 3-Nitrobenzaldehyde (3.02 g; 0.02 mol), ethyl acetoacetate (2.6 g; 0.02 mol), 1-methyl-3-phenyl-5-pyrazolamine (3.46 g; 0.02 mol) in absolute ethanol (30 ml) are refluxed under nitrogen and in the darkness. After about 5 hours, the mixture is cooled to 0° C. and the insolubles are collected by filtration and discarded. The filtrate is concentrated under reduced pressure, the residue is dissolved in ethyl ether and the product of the title is precipitated by addition of hydrogen chloride/ethyl ether. The collected solid can be further purified by making a suspension of it in water, alkalinizing the pH with NaHCO$_3$, extracting with ethyl ether and precipitating with hydrogen chloride ether. M.p. 212°-215° C.

EXAMPLE 58

Preparation of 1-methyl-3-(1-methylethyl)-5(1H)-pyrazolamine

4-Methyl-3-oxo-pentanenitrile (39.58 g; 0,356 mol) dissolved in glacial acetic acid (400 ml) and methylhydrazine (18.05 g; 0.382 mol) is added thereto, at 15°-20° C.

The reaction mixture is heated to 70°-75° C. under nitrogen stream for about 5 hours. Then the mixture is cooled, and the solvent is evaporated under reduced pressure. The residue is taken up with water (200 ml) and the pH adjusted to about 9. After extraction with methylene chloride, the solvent of the dried organic layer is stripped off. The residue is taken up in ethyl ether and recovered by filtration. M.p. 115°-118° C.

EXAMPLE 59

Preparation of N-benzyl-1,3-dimethyl-5(1H)-pyrazolamine.

A mixture of 1,3-dimethyl-5(1H)-pyrazolamine (2 mmol) and benzylchloride (2 mmol) in methylene chloride (10 ml) in the presence of triethylamine (1 ml) is heated to the reflux temperature, for about 6 hours. The reaction mixture is then cooled, washed with water and the organic solvent is evaporated to dryness. The compound of the title crystallizes out from a mixture ethyl ether/petroleum ether. M.P. 95°-97° C.

I claim:

1. A 4,7-dihydropyrazolo[3,4-b]pyridine-5-carboxylic acid compound of the formula:

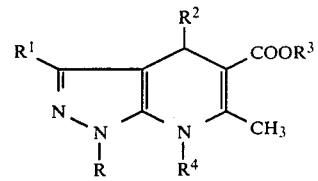

wherein R represents a methyl group; R$^1$ represents a C$_4$ alkyl group; R$^2$ represents a 2-methylphenyl group; R$^3$ represents a methyl group; and R$^4$ represents hydrogen; or a physiologically acceptable salt thereof.

2. A 4,7-dihydropyrazolo[3,4-b]pyridine-5-carboxylic acid compound of claim 1 wherein R$^1$ is a 2-methylpropyl group.

3. The hydrochloride salt of the 4,7-dihydropyrazolo[3,4-b]pyridine-5-carboxylic acid compound of claim 2.

4. A method for the treatment of hypertension in a patient in need thereof which comprises administering to said patient an antihypertensive effective amount of a compound of claim 1.

5. A method of claim 4 wherein in the active compound $R^1$ is a 2-methylpropyl group or the hydrochloride salt thereof.

6. A pharmaceutical composition for the treatment of hypertension and/or angina in dosage unit form comprising an amount of from 0.05 to 100 mg of a compound of claim 1 and a pharmaceutical carrier.

7. A composition of claim 6 wherein $R^1$ is a 2-methylpropyl group or the hydrochloride salt thereof.

* * * * *

UNITED STATES PATENT AND TRADEMARK OFFICE
CERTIFICATE OF CORRECTION

PATENT NO.   : 4,954,508

DATED        : September 4, 1990

INVENTOR(S)  : Giorgio Winters

It is certified that error appears in the above-identified patent and that said Letters Patent is hereby corrected as shown below:

At Column 7, lines 50-51, patent reads "polyoxyethylenglycols" and should read --polyoxyethyleneglycols--.

At Column 8, line 18, patent reads "sugar" and should read --A sugar--.

At Column 13, line 48, patent reads "ehtyl" and should read --ethyl--.

Signed and Sealed this

Eighth Day of December, 1992

*Attest:*

DOUGLAS B. COMER

*Attesting Officer*   *Acting Commissioner of Patents and Trademarks*